(12) United States Patent
Mou et al.

(10) Patent No.: US 11,540,416 B2
(45) Date of Patent: Dec. 27, 2022

(54) ACTUATING BREATHABLE MATERIAL STRUCTURE

(71) Applicant: Microjet Technology Co., Ltd., Hsinchu (TW)

(72) Inventors: Hao-Jan Mou, Hsinchu (TW); Ta-Wei Hsueh, Hsinchu (TW); Yung-Lung Han, Hsinchu (TW); Chi-Feng Huang, Hsinchu (TW); Chun-Yi Kuo, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 467 days.

(21) Appl. No.: 16/728,913

(22) Filed: Dec. 27, 2019

(65) Prior Publication Data

US 2020/0229320 A1    Jul. 16, 2020

(30) Foreign Application Priority Data

Jan. 11, 2019 (TW) ................................. 108101266
Jan. 11, 2019 (TW) ................................. 108101267

(Continued)

(51) Int. Cl.
*H05K 7/20* (2006.01)
*A41D 13/002* (2006.01)
*G06F 1/16* (2006.01)
*G06F 1/20* (2006.01)
(Continued)

(52) U.S. Cl.
CPC ....... *H05K 7/20145* (2013.01); *A41D 13/002* (2013.01); *G06F 1/163* (2013.01);
(Continued)

(58) Field of Classification Search
CPC ........... H05K 7/20145; H05K 7/20209; H05K 7/20127; G06F 1/163; A41D 13/002; A41D 1/002; A61B 5/021; A61B 5/14532
See application file for complete search history.

(56) References Cited

U.S. PATENT DOCUMENTS

2006/0267167 A1* 11/2006 McCain .................. H04B 1/04
                                                             257/678
2017/0047769 A1*  2/2017 Kim ...................... H02J 7/0042
(Continued)

FOREIGN PATENT DOCUMENTS

CN       202890548 U     4/2013
CN       207721239 U     8/2018
(Continued)

OTHER PUBLICATIONS

Taiwanese Office Action and Search Report, dated Mar. 31, 2020, for Taiwanese Application No. 108101268.
(Continued)

*Primary Examiner* — Mukundbhai G Patel
(74) *Attorney, Agent, or Firm* — Birch, Stewart, Kolasch & Birch, LLP (57) ABSTRACT

An actuating breathable material structure is disclosed and includes a supporting main body, a plurality of actuating breathable units and a plurality of micro processing chips. The supporting main body is made of a supporting matrix. The plurality of actuating breathable units and the plurality of micro processing chips are compounded and are integrally formed with the supporting matrix into one piece. By controlling the actuation of the plurality of actuating breathable units through the plurality of micro processing chips, a breathing effect resulting from gas transportation in a specific direction is performed.

20 Claims, 11 Drawing Sheets

| (30) | Foreign Application Priority Data | | |
|---|---|---|---|
| Jan. 11, 2019 | (TW) | ................................. | 108101268 |
| Jan. 11, 2019 | (TW) | ................................. | 108101269 |

(51) Int. Cl.
    *A41D 1/00*           (2018.01)
    *A61B 5/021*         (2006.01)
    *A61B 5/145*         (2006.01)
    *A41D 1/06*          (2006.01)

(52) U.S. Cl.
    CPC ............ *G06F 1/1635* (2013.01); *G06F 1/203* (2013.01); *G06F 1/206* (2013.01); *H05K 7/20209* (2013.01); *A41D 1/002* (2013.01); *A41D 1/06* (2013.01); *A61B 5/021* (2013.01); *A61B 5/14532* (2013.01); *H05K 7/20127* (2013.01)

(56) References Cited

U.S. PATENT DOCUMENTS

2017/0292537 A1\* 10/2017 Barak ................ H05K 7/20172
2017/0369305 A1\* 12/2017 Suvanto ................ H04R 1/326

FOREIGN PATENT DOCUMENTS

| CN | 208188080 U | 12/2018 |
|---|---|---|
| CN | 208350735 U | 1/2019 |
| CN | 210726724 U | 6/2020 |
| EP | 2 873 915 A2 | 5/2015 |
| TW | M248331 U | 11/2004 |
| TW | M251937 U | 12/2004 |
| TW | M553321 U | 12/2017 |
| TW | M554513 U | 1/2018 |
| TW | M555406 U | 2/2018 |
| TW | M555407 U | 2/2018 |
| TW | M557256 U | 3/2018 |
| TW | M559312 U | 5/2018 |
| TW | M560894 U | 6/2018 |
| TW | 201831788 A | 9/2018 |
| WO | WO 2018/009164 A1 | 1/2018 |

OTHER PUBLICATIONS

Taiwanese Office Action and Search Report, dated May 12, 2020, for Taiwanese Application No. 1081010269.

\* cited by examiner

ACTUATING BREATHABLE MATERIAL STRUCTURE

FIELD OF THE INVENTION

The present disclosure relates to an actuating breathable material structure, and more particularly to an actuating breathable material structure having a function of gas transportation in a specific direction.

BACKGROUND OF THE INVENTION

For some products that require the functions of breathability and ventilation, such as some clothing or the electronic products (such as notebook), heat is generated therefrom and has to be dissipated. How to make these products have the functions of breathability and ventilation is a key aspect of the present disclosure. Therefore, how to develop an actuating breathable material structure applied to those products and having the function of gas transportation in a specific direction is the main subject of the present disclosure.

SUMMARY OF THE INVENTION

An object of the present disclosure is to provide an actuating breathable material structure. By compounding a miniaturized actuating breathable unit in a supporting matrix of a supporting main body, the actuating breathable material structure is formed, so as to be applied to the product which requires the functions of breathability and ventilation.

Another object of the present disclosure is to provide an actuating breathable material structure. A plurality of actuating breathable units are compounded in the supporting matrix and integrally formed with the supporting matrix. While the plurality of actuating breathable units are driven to work, a breathing effect resulting from gas transportation in a specific direction is achieved in the supporting matrix.

In accordance with an aspect of the present disclosure, an actuating breathable material structure is provided and includes a supporting main body made of a supporting matrix; a plurality of actuating breathable units; and a plurality of micro processing chips. The plurality of actuating breathable units and the plurality of micro processing chips are compounded in the supporting matrix and integrally formed with the supporting matrix in one piece, wherein the plurality of actuating breathable units are controlled by the plurality of micro processing chips to perform gas transportation in a specific direction, and a breathing effect of the supporting main body is performed.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
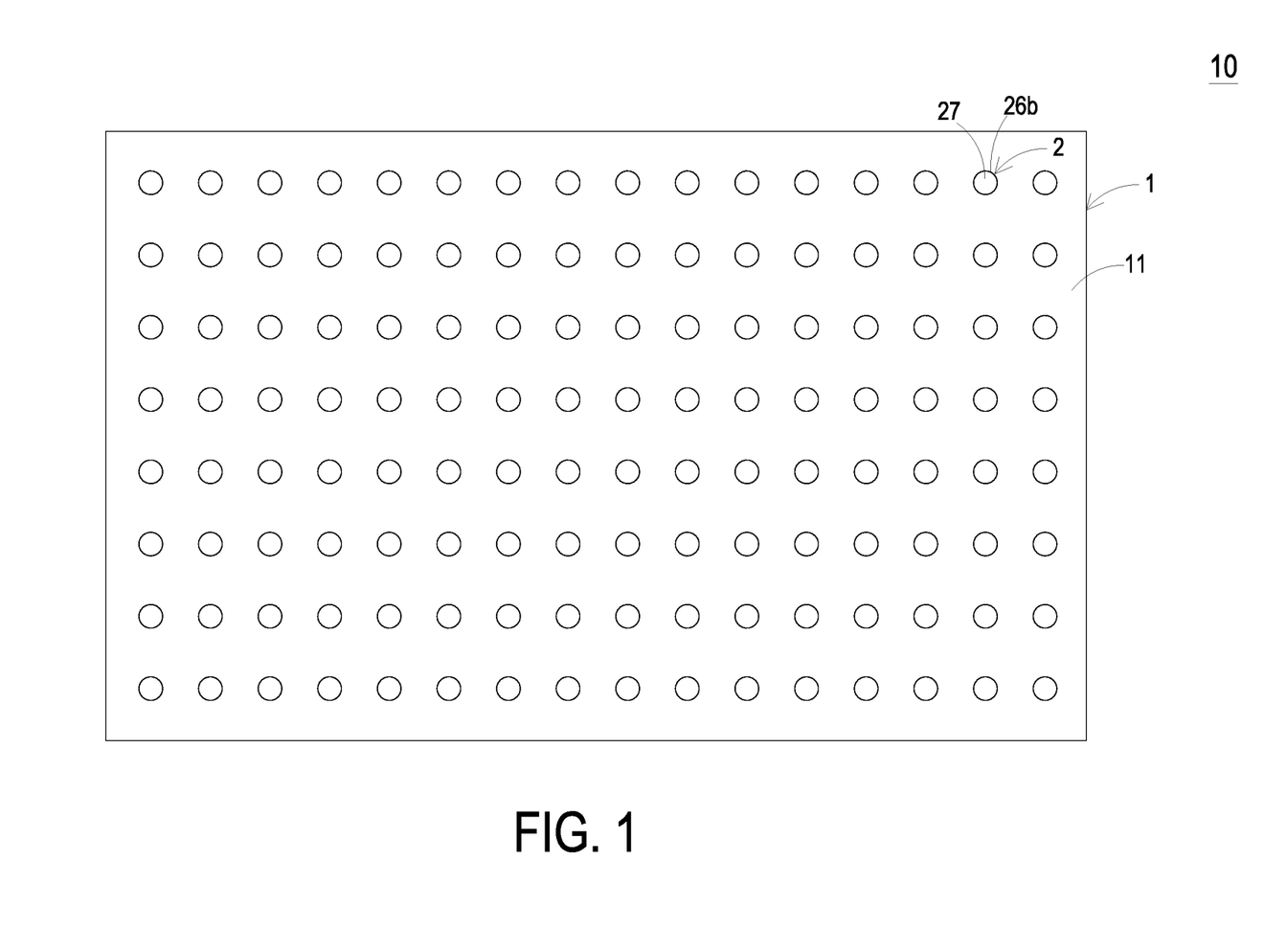
FIG. 1 schematically illustrates an actuating breathable material structure according to an embodiment of the present disclosure.
Figure 2:
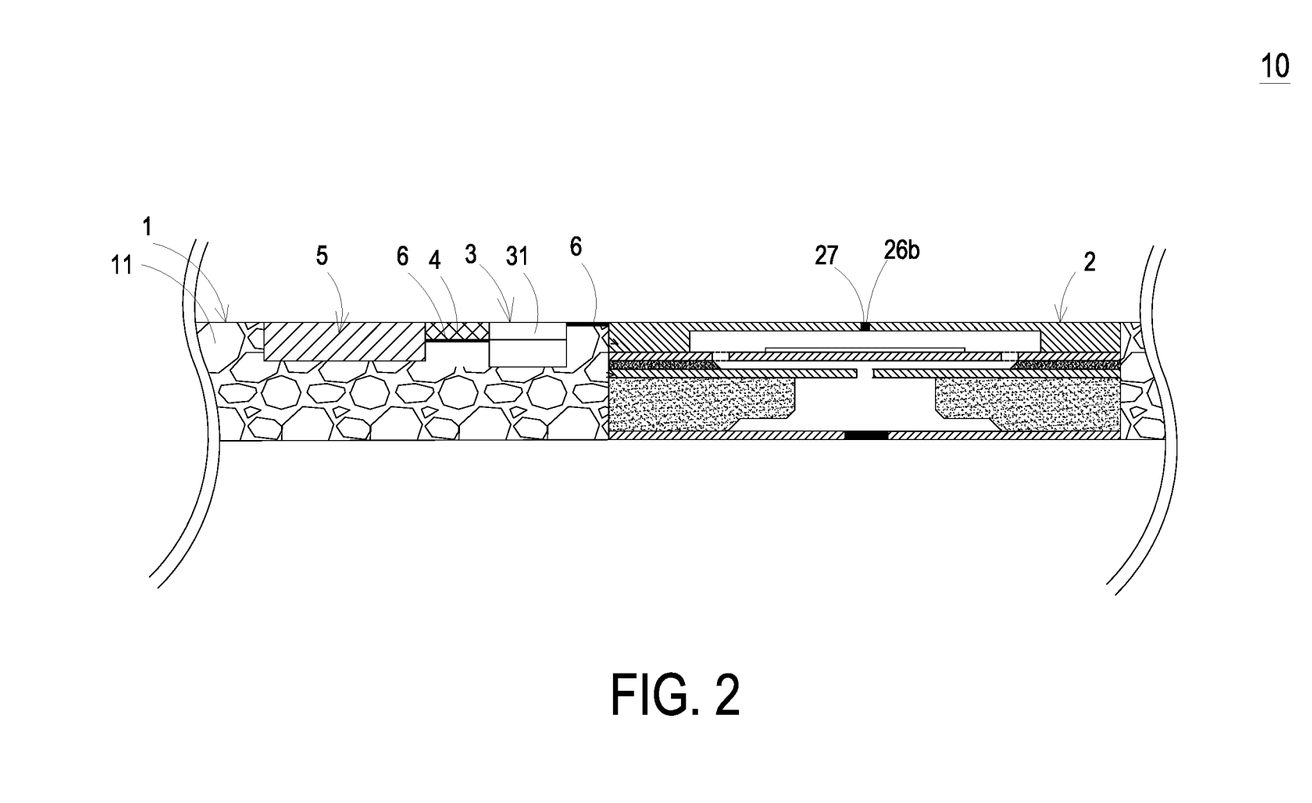
FIG. 2 is a schematic cross-sectional view illustrating the actuating breathable material structure of FIG. 1.

Please refer to FIGS. 1 and 2. The present discourse provides an actuating breathable material structure 10 including a supporting main body 1, a plurality of actuating breathable units 2, a plurality of micro processing chips 3, a plurality of sensors 4 and a plurality of power supply units 5. In the embodiment, the supporting main body 1 is made of a supporting matrix 11. The plurality of actuating breathable units 2 are compounded in the supporting matrix 11 of the supporting main body 1, and integrally formed with the supporting matrix 11 in one piece. The plurality of actuating breathable units 2 are driven to perform gas transportation in a specific direction and a breathing effect of the supporting main body 1 is achieved. The plurality of micro processing chips 3 are embedded in a surface of the supporting matrix 11 of the supporting main body 1, so as to control operations of the plurality of actuating breathable units 2. The plurality of sensors 4 are embedded in the surface of the supporting matrix 11 of the supporting man body 1 for electrical connection with the plurality of micro processing chips 3. Moreover, detection data from the plurality of sensors 4 is accessible to the plurality of micro processing chips 3 for transmission. The plurality of sensors 4 detect humidity and temperature outside the supporting matrix 11 of the supporting main body 1 and the detection data is provided to the plurality of micro processing chips 3. Thus, the plurality of actuating breathable units 2 are controlled by the plurality of micro processing chips 3 to perform the gas transportation in the specific direction, and the breathing effect of the supporting main body 1 is achieved. In the embodiment, each of the plurality of micro processing chips 3 includes a data transmission component 31, which receives the detection data from the plurality of sensors 4 and transmits the detection data to an external receiving device. In that, the external receiving device displays the detection data of the sensors 4. More specifically, the external receiving device is capable of visualizing the detection data of the sensors 4, and displays information carried by the detection data. In the embodiment, the external receiving device is a mobile communication device, but the present disclosure is not limited thereto. The plurality of power supply units 5 are embedded in the surface of the supporting matrix 11 of the supporting main body 1 to output power through the conductive wire 6 to the plurality of actuating breathable units 2 and the plurality of micro processing chips 3 for driving operation. In an embodiment, the power supply unit 5 is an energy-absorbing electric board, which converts optical energy into electrical energy for outputting, but the present disclosure is not limited thereto. In another embodiment, the power supply unit 5 is a graphene battery, but the present disclosure is not limited thereto.

In the embodiment, the supporting matrix 11 may be a raw material, which is a naturally occurring and unprocessed substance; or the supporting matrix 11 may be an intermediate material, which is a processed substrate formed after processing the raw material. The material of the supporting matrix 11 may be an organic material or an inorganic material, classified from a chemical perspective; the material of the supporting matrix 11 may be at least one selected from the group consisting of a metal material, a polymer material, a ceramic material, and a composite material, classified from an engineering perspective; or the material of the supporting matrix 11 may be at least one selected from the group consisting of a building material, an electronic material, an aviation material, an automotive material, an energy material and a biomedical material, classified from an application perspective. The present disclosure is not limited thereto.

Figure 3A:
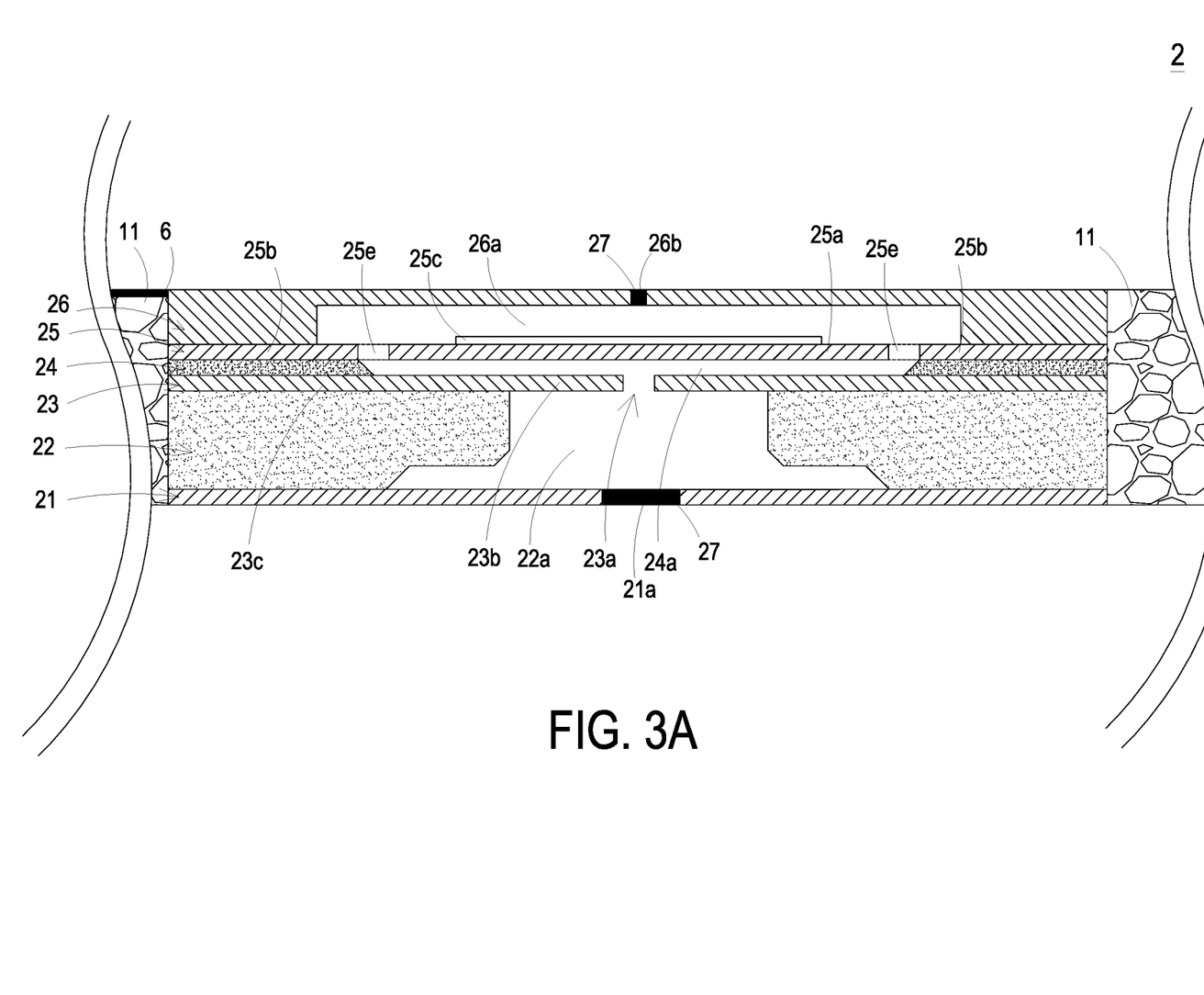
FIG. 3A is a schematic cross-sectional view illustrating an actuating breathable unit according to an embodiment of the present disclosure.

Please refer to FIG. 3A. In the embodiment, each of the plurality of actuating breathable units 2 includes an inlet layer 21, a flow channel layer 22, a resonance layer 23, a chamber layer 24, an actuating layer 25, an outlet layer 26 and a plurality of valves 27, which are stacked on each other sequentially. The plurality of actuating breathable units 2 are made through a micro-electromechanical (MEMS) process. In an embodiment, the actuating breathable unit 2 is manufactured from a micro structural material, and the actuating breathable unit 2 has a size ranging from 1 μm to 999 μm. In another embodiment, the actuating breathable unit 2 is manufactured from a nano structural material, and the actuating breathable unit 2 has a size ranging from 1 nm to 999 nm. The present disclosure is not limited thereto.

Figure 3B:
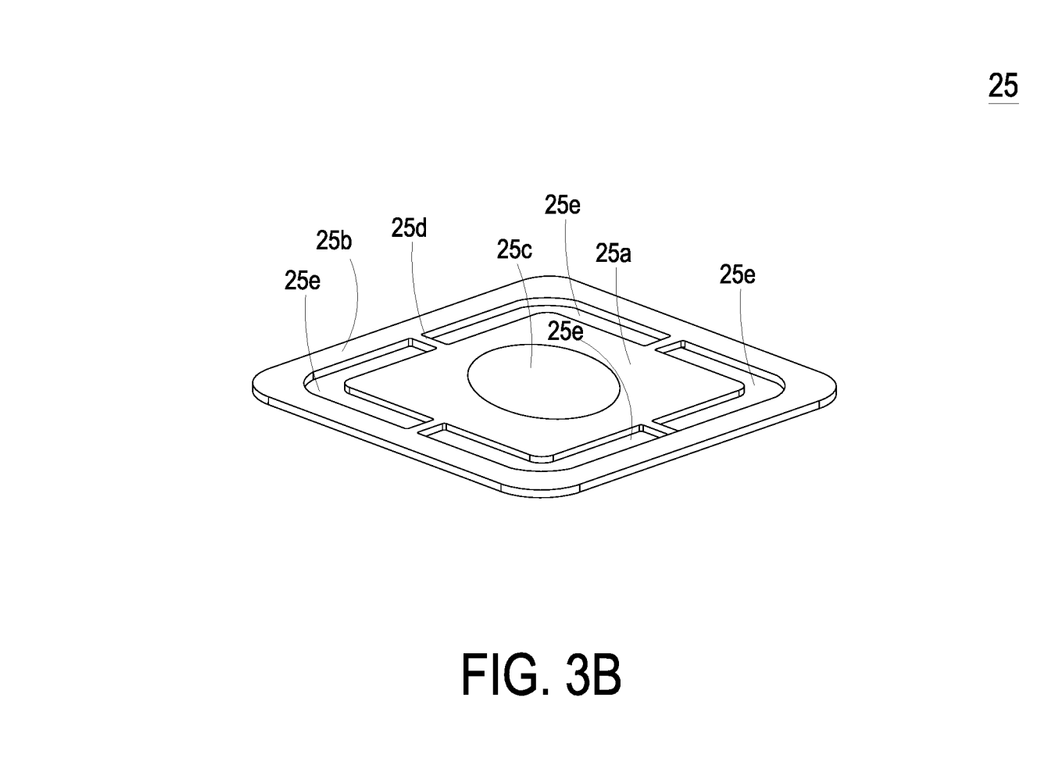
FIG. 3B is a schematic structural view illustrating an actuating layer of the actuating breathable unit according to an embodiment of the present disclosure.

In the embodiment, the inlet layer 21 includes an inlet aperture 21a formed at the center of the inlet layer 21. In the embodiment, the flow channel layer 22 is stacked on and connected with the inlet layer 21, and has a communication channel 22a. The communication channel 22a spatially corresponds to the inlet aperture 21a of the inlet layer 21, and in fluid communication with the inlet aperture 21a. In the embodiment, the resonance layer 23 is stacked on and connected with the flow channel layer 22, and has a central aperture 23a, a movable part 23b and a fixed part 23c. The central aperture 23a is disposed at the center of the resonance layer 23, spatially corresponds to the communication channel 22a of the flow channel layer 22, and is in fluid communication with the communication channel 22a. The movable part 23b is disposed around the central aperture 23a and is a part of the resonance layer 23 that is not contacted with the flow channel layer 22, so as to form a flexible structure. The fixed part 23c is located at a part of the resonance layer 23 that is contacted with the flow channel layer 22. In the embodiment, the chamber layer 24 is stacked on and connected with the resonance layer 24. The center of the chamber layer 24 is hollowed out to form a resonance chamber 24a. As shown in the drawings, the chamber layer 24 is stacked on and connected with the fixed part 23c of the resonance layer 23, and the resonance chamber 24a spatially corresponds to the central aperture 23a of the resonance layer 23 and is in fluid communication with the central aperture 23a. In the embodiment, the actuating layer 25 is stacked on and connected with the chamber layer 24. As shown in FIG. 3B, the actuating layer 25 is a hollow suspension structure and includes a vibration region 25a, an outer region 25b, an actuator 25c, a plurality of connecting regions 25d and a plurality of vacant spaces 25e. The vibration region 25a is connected to the outer region 25b through the plurality of connecting regions 25d, so that the plurality of connecting regions 25d elastically support the vibration region 25a to allow the vibration region 25a to be elastically displaced. In the embodiment, the vibration region 25a has a square outline, but the present disclosure is not limited thereto. The plurality of vacant spaces 25e are defined between the vibration region 25a and the outer region 25b for allowing the gas to flow therethrough. In other embodiment, the way of disposition, the types and the numbers of the vibration region 25a, the outer region 25b, the plurality of connecting regions 25d and the plurality of vacant spaces 25e may be varied according to the practical requirements, but not limited thereto. In the embodiment, the actuator 25c is disposed on a surface of the vibration region 25a. When the actuator 25c is driven in response to an applied voltage, which is controlled and provided by the micro processing chip 3 through the conductive wire 6, and undergoes a bending deformation to drive the vibration region 25a to vibrate along a vertical direction in a reciprocating manner. In the embodiment, the actuator 25c has a circular outline, but the present disclosure is not limited thereto. In the embodiment, the outlet layer 26 is stacked on and connected with the outer region 25b of the actuating layer 25 to cover the actuator 25c of the actuating layer 25. An outlet chamber 26a is formed between outlet layer 26 and the actuating layer 25. The outlet layer 26 has an outlet aperture 26b. The outlet aperture 26b is in fluid communication with the outlet chamber 26a, and the outlet chamber 26a is in fluid communication with the resonance chamber 24a of the chamber layer 24 through the plurality of vacant spaces 25e of the actuating layer 25. In the embodiment, each of the plurality of valves 27 is disposed in the outlet aperture 26b of the outlet layer 26 and the inlet aperture 21a of the inlet layer 21 to control the fluid communication of the inlet aperture 21a and the outlet aperture 26b.

Figure 5A:
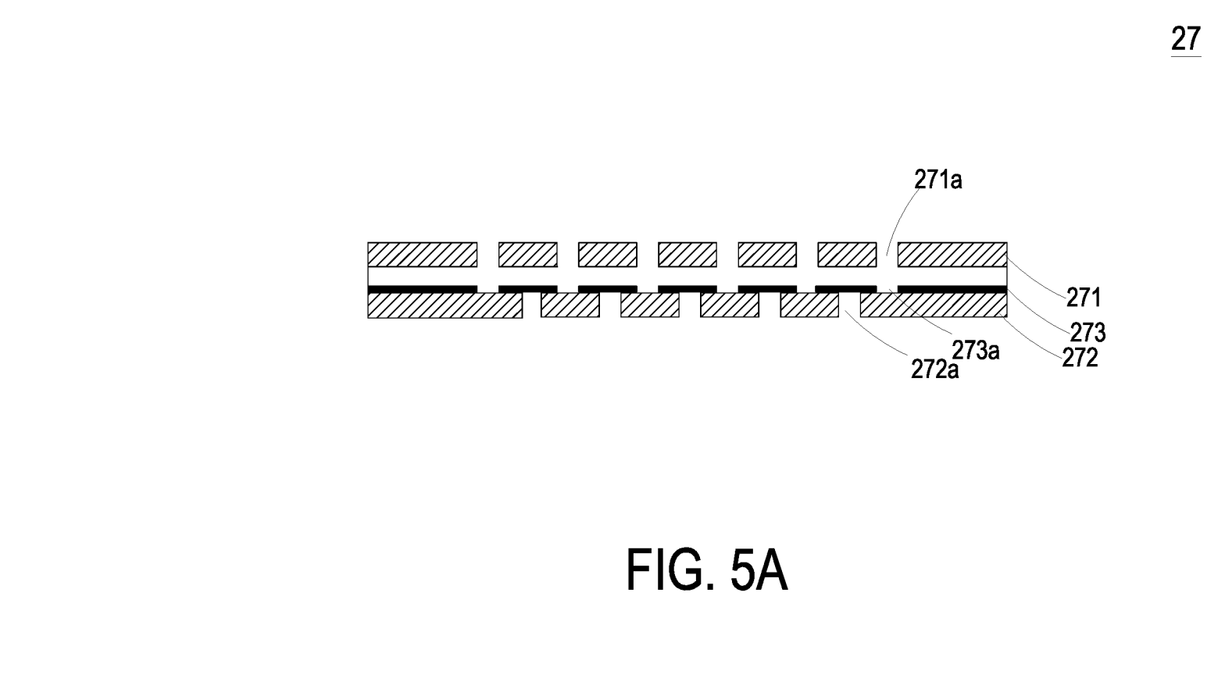
FIGS. 5A and 5B are schematic cross-sectional views illustrating the actions of the valve used in the actuating breathable unit according to an embodiment of the present disclosure.
Figure 5B:
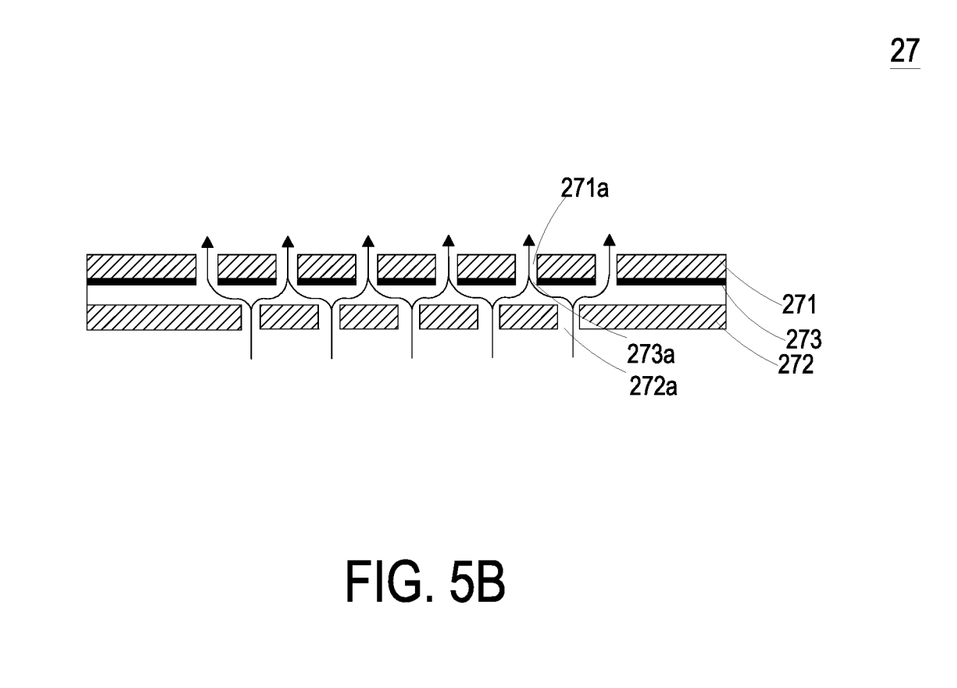

Please refer to FIG. 5A. In the embodiment, the valve 27 includes a stationary component 271, a sealing component 272 and a displacement component 273. The displacement component 273 is disposed between the stationary component 271 and the sealing component 272 and capable of displacing therebetween. The stationary component 271 has a plurality of first orifices 271a. The displacement component 273 has a plurality of second orifices 273a respectively corresponding in position to the plurality of first orifices 271a of the stationary component 271. That is, the plurality of first orifices 271a of the stationary component 271 are aligned with the plurality of second orifices 273a of the displacement component 273. The sealing component 272 has a plurality of third orifices 272a. The plurality of third orifices 272a of the sealing component 272 are misaligned with the plurality of first orifices 271a of the stationary component 271. In the embodiment, the displacement component 273 is made of a charged material, and the stationary component 271 is made of a bipolar conductive material. The polarities of the displacement component 273 and the stationary component 271 are controlled by the micro processing chip 3 (as shown in FIG. 2). When the displacement component 273 and the stationary component 271 are maintained in the same polarity, the displacement component 273 moves toward the sealing component 272 and the valve 27 is in a closed state. Please refer to FIG. 5B. In the embodiment, the displacement component 273 is made of a charged material, and the stationary component 271 is made of a bipolar conductive material. The polarities of the displacement component 273 and the stationary component 271 are controlled by the micro processing chip 3 (as shown in FIG. 2). In case that the displacement component 273 and the stationary component 271 are maintained in the opposite polarity, the displacement component 273 moves toward the stationary component 271 and the valve 27 is in an open state. Accordingly, by adjusting the polarity of the stationary component 271, the displacement component 273 is moved to control the valve 27 in the open/closed state. Moreover, in another aspect of the valve 27 in the present disclosure, the displacement component 273 is made of a magnetic material, and the stationary component 271 is made of an electromagnet material and can be controlled to change its magnetic polarity. When the displacement component 273 and the stationary component 271 are maintained in the same polarity, the displacement component 273 moves toward the sealing component 272 and the valve 27 is in a closed state. Alternatively, when the displacement component 273 and the stationary component 271 are maintained in the opposite polarity, the displacement component 273 moves toward the stationary component 271 and the valve 27 is in an open state. According to the above descriptions, by adjusting the magnetic polarity of the stationary component 271, the displacement component 273 is moved to control the valve 27 in the open/closed state. The magnetic polarity of the stationary component 271 is controlled by the micro processing chip 3 (as shown in FIG. 2).

Figure 3C:
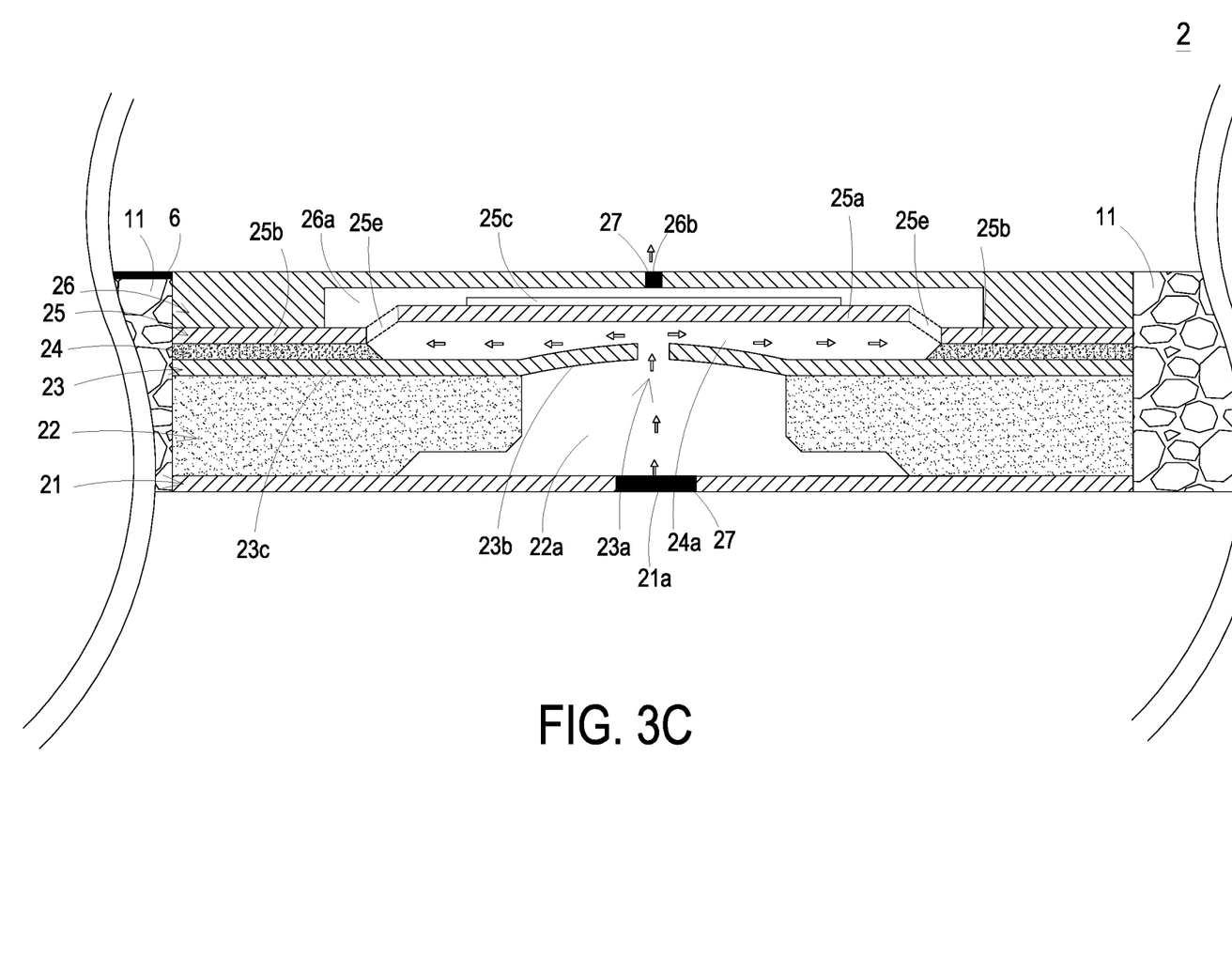
FIGS. 3C and 3D schematically illustrate the actions of the actuating breathable of FIG. 3A.
Figure 3D:
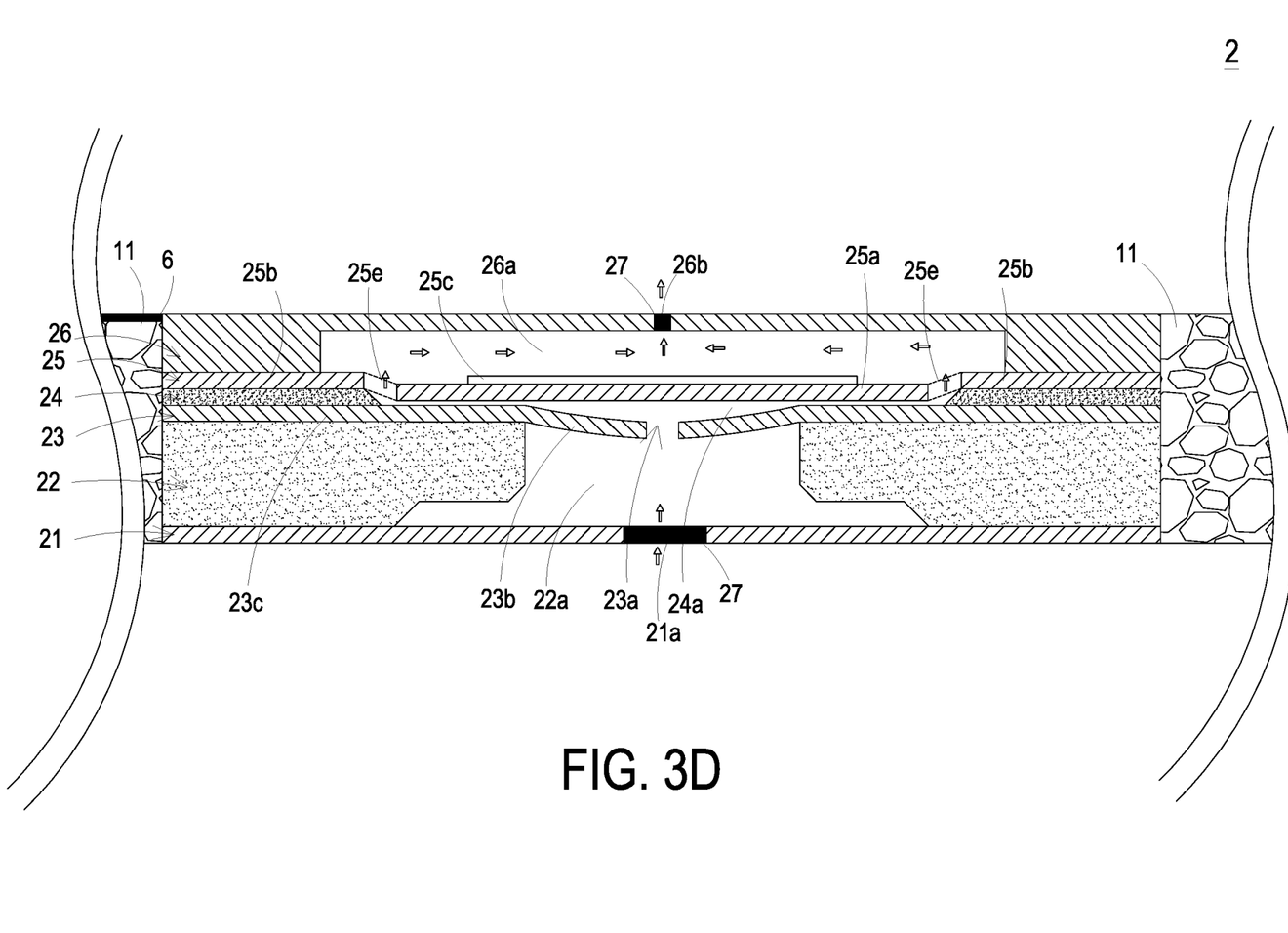

Please refer to FIGS. 3C to 3D. When the actuator 25c is driven in response to an applied voltage, which is controlled and provided by the micro processing chip 3 through the conductive wire 6, the actuator 25c undergoes a bending deformation to drive the vibration region 25a to vibrate along a direction vertical to the surface of the vibration region 25a in a reciprocating manner. As shown in FIG. 3C, when the actuator 25c is driven in response to an applied voltage controlled and provided by the micro processing chip 3 through the conductive wire 6 and undergoes a bending deformation to drive the vibration region 25a to move in a direction away from the inlet layer 21, and the valves 27 are controlled in an open state by the micro processing chip 3 (as shown in FIG. 2), the vibration region 25a is displaced in the direction away from the inlet layer 21 in response to the vibration due to the deformation. Moreover, the movable part 23b of the resonance layer 23 is driven to move in the direction away from the inlet layer 21, so that the volume of the resonance chamber 24a of the chamber layer 24 is enlarged and a suction force is generated. In that, gas is inhaled through the inlet aperture 21a of the inlet layer 21, flows through the valve 27 in the inlet layer 21, is converged in the communication channel 22a of the flow channel layer 22 and is transported into the resonance chamber 24a through the central aperture 23a of the resonance layer 23 for storing temporarily. Thereafter, as shown in FIG. 3D, when the actuator 25c is driven in response to the applied voltage controlled and provided by the micro processing chip 3 through the conductive wire 6 and undergoes a bending deformation to drive the vibration region 25a to move in a direction toward the inlet layer 21, the vibration region 25a of the actuating layer 25 is displaced in the direction toward the inlet layer 21 in response to the vibration due to the deformation of the actuator 25c. In that, the resonance chamber 24a of the chamber layer 24 is compressed by the vibration region 25a of the actuating layer 25 to reduce the volume thereof, and the gas in the resonance chamber 24a is compressed toward the periphery and flows into the outlet chamber 26a through the plurality of vacant spaces 25e. Please refer to FIG. 3C, again. When the actuator 25c is driven in response to the applied voltage provided by the electrical energy outputted from the power supply unit 5 through the conductive wire 6 and undergoes a bending deformation to move in a direction away from the inlet layer 21, the vibration region 25a is displaced in the direction away from the inlet layer 21 in response to the vibration due to the deformation of the actuator 25c. In that, the gas in the outlet chamber 26a flows through the valve 27 in the outlet layer 26, and is discharged to the outside of the outlet layer 26 through the outlet aperture 26b of the outlet layer 26. Consequently, the gas is transported in the specific direction and the breathing effect of the supporting main body 1 is achieved. In such way, by performing the above actions and steps illustrated in FIGS. 3C and 3D repeatedly, the gas is continuously inhaled into the inlet aperture 21a to be pressurized and discharged out through the outlet aperture 26b.

In the embodiment, the vibration frequency of the resonance layer 23 along the vertical direction in the reciprocating manner may be identical to the vibration frequency of the vibration region 25a of the actuating layer 25. That is, the resonance layer 23 and the vibration region 25a synchronously vibrate along the upward direction or the downward direction. It should be noted that numerous modifications and alterations of the actions of the actuating breathable unit 2 may be made while retaining the teachings of the disclosure. In this embodiment, the actuating breathable unit 2 generates a pressure gradient in the flow channels of itself to facilitate the gas to flow at a high speed. Since there is an impedance difference between the inlet direction and the outlet direction, the gas can be transported from the inlet aperture 21a to the outlet aperture 26b. Moreover, even if a gas pressure exists at the discharge end of the outlet aperture 26b, the actuating breathable unit 2 still has the capability to discharge out the gas while achieving the silent efficacy.

Figure 4A:
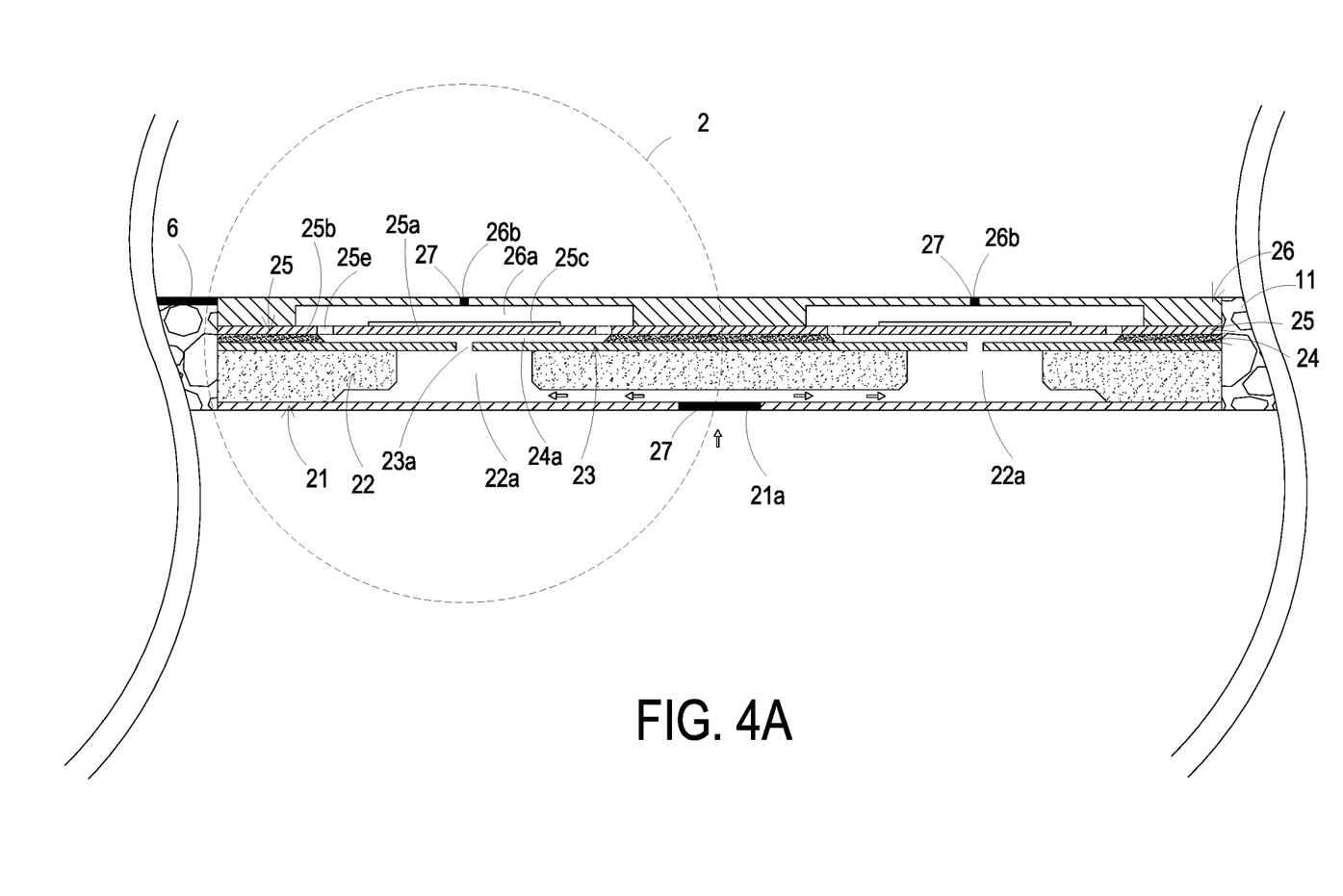
FIG. 4A schematically illustrates a portion of the actuating breathable material structure, in which the actuating breathable units are connected with each other in a serial arrangement.
Figure 4B:
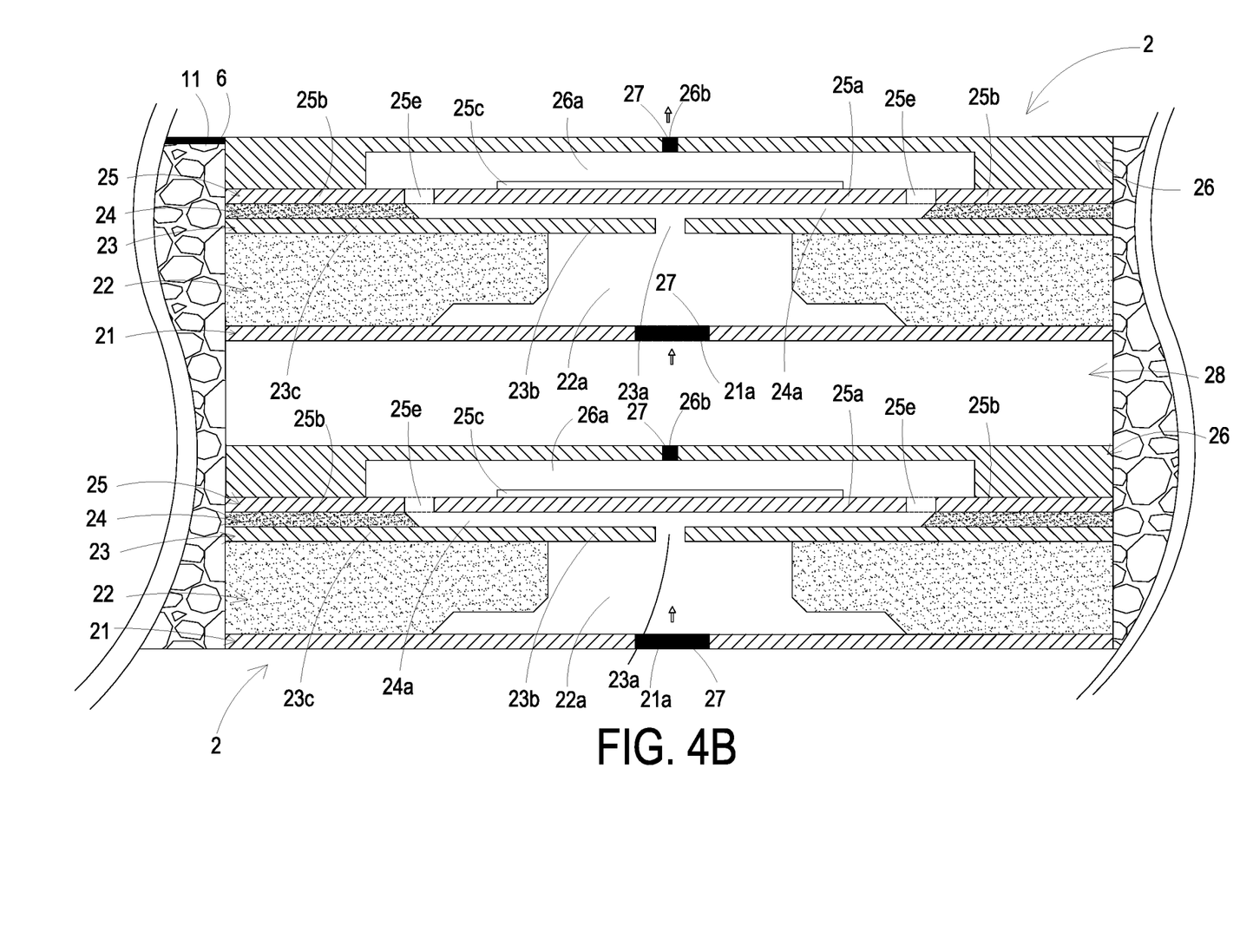
FIG. 4B schematically illustrates a portion of the actuating breathable material structure, in which the actuating breathable units are connected with each other in a parallel arrangement.
Figure 4C:
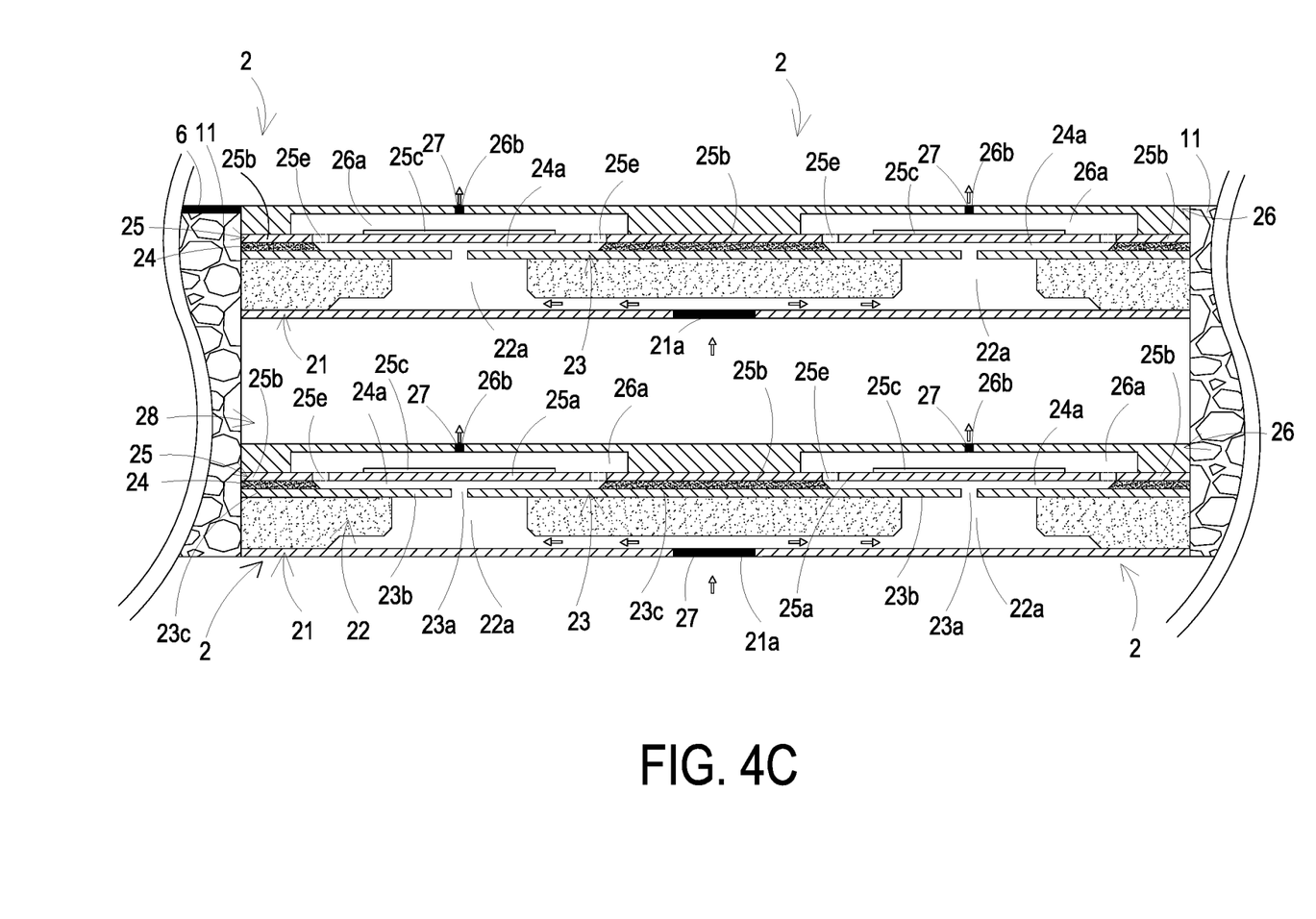
FIG. 4C schematically illustrates a portion of the actuating breathable material structure, in which the actuating breathable units connected with each other in a serial-and-parallel arrangement.

Please refer to FIGS. 4A to 4C. In the embodiment, the plurality of actuating breathable units 2 are compounded in the supporting matrix 11 of the supporting main body 1, and integrally formed with the supporting matrix 11 in one piece. The plurality of actuating breathable units 2 are disposed in a specific arrangement to adjust the total amount and the flow rate of gas transportation outputted by the actuating breathable material structure 10. As shown in FIG. 4A, in the embodiment, the plurality of actuating breathable units 2 share an inlet layer 21, a flow channel layer 22, a resonance layer 23, a chamber layer 24, an actuating layer 25 and an outlet layer 26. Two sets of the actuating breathable units 2 share an inlet aperture 21a of the inlet layer 21, and are disposed in a parallel arrangement, which is implemented through the MEMS process. In that, the plurality of actuating breathable units 2 are disposed in a serial arrangement, so as to increase the total amount of gas transportation outputted by the actuating breathable material structure 10. As shown in FIG. 4B, in the embodiment, the plurality of actuating breathable units 2 have each two of actuating breathable units 2 stacked with each other through the MEMS process. A common chamber 28 is formed between the two actuating breathable units 2 and in fluid communication therebetween. In that, the plurality of actuating breathable units 2 are disposed in a parallel arrangement, so as to increase the flow rate of gas transportation outputted by the actuating breathable material structure 10. As shown in FIG. 4C, in the embodiment, the plurality of actuating breathable units 2 have a set of two actuating breathable units 2 disposed in a serial arrangement, and another set of two actuating breathable units 2 disposed in a serial arrangement, which are stacked with each other. A common chamber 28 is formed between the two sets of actuating breathable units 2 and in fluid communication therebetween. In this way, one set of serial actuating breathable units 2 and the other set of serial actuating breathable units 2 are arranged in parallel. In that, the plurality of actuating breathable units 2 are stacked and disposed in a serial-and-parallel arrangement through the MEMS process, so as to increase the total amount and the flow rate of gas transportation outputted by the actuating breathable material structure 10. In the embodiment, the plurality of actuating breathable units 2 have high flexibility in assembling arrangement as long as being connected with the driving circuit, and the actuating breathable units 2 may be enabled to transport the gas simultaneously so as to transport a great amount of gas according to the practical requirements. In addition, each actuating breathable unit 2 may be individually controlled to be enabled or disabled. For example, one actuating breathable unit 2 is enabled, and the other actuating breathable unit 2 is disabled. Another example is that the actuating breathable unit 2 are alternately enabled, but not limited thereto. Consequently, the purpose of transporting various amount of the gas and the purpose of reducing the power consumption is achieved.

Notably, in the embodiment, the plurality of actuating breathable units 2 may be uniformly disposed and compounded in the supporting matrix 11 of the supporting main body 1, and are integrally formed with the supporting matrix 11 in one piece. Namely, the plurality of actuating breathable units 2 are uniformly distributed in and integrally formed with the supporting matrix 11 in one piece. Alternatively, the plurality of actuating breathable units 2 may be unevenly disposed and compounded in the supporting matrix 11 of the supporting main body 1, and are integrally formed with the supporting matrix 11 in one piece. Namely, the plurality of actuating breathable units 2 are compounded in a specific region of and integrally formed with the supporting matrix 11 in one piece. The arrangement of the plurality of actuating breathable units 2 disposed within the supporting matrix 11 is adjustable according the design requirements. The present disclosure is not limited thereto.

Notably, in the embodiment, as mentioned above, the supporting matrix 11 of the supporting main body 1 can be made of a variety of raw materials or intermediate materials. In order to compound a plurality of actuating breathable units 2 in the supporting matrix 11 of the supporting main body 1 to form an actuating breathable material structure 10, there are a lot of methods provided in response to different raw materials and intermediate materials. For example, when the supporting matrix 11 is a metal material, a ceramic material or the like, a method of mixing the plurality of actuating breathable units 2 into the supporting matrix 11 for compounding can be utilized; when the supporting matrix 11 is a fiber material, a textile material or the like, a method of weaving the plurality of actuating breathable units 2 into the supporting matrix 11 for compounding can be utilized; when the supporting matrix 11 is a polymer material, a method of implanting the plurality of actuating breathable units 2 into the supporting matrix 11 for compounding can be utilized.

The method of compounding the plurality of actuating breathable units 2 in the supporting matrix 11 of the supporting main body 1 is adjustable according to the practical requirements. The present disclosure is not limited thereto.

From the above description, it is known that the actuating breathable material structure 10 of the present disclosure is applicable of practical implementations. When the actuating breathable material structure 10 is implemented as a textile material for wearing clothes, the plurality of actuating breathable units 2 are compounded in the supporting matrix 11 (such as the textile material) of the supporting main body 1 by the method of weaving the plurality of actuated ventilating units 2 into the supporting matrix 11 (such as the textile material). Moreover, the plurality of micro processing chips 3, the plurality of sensors 4 and the plurality of power supply units 5 are woven and composed in the supporting matrix 11 (such as the textile material), so as to form the actuating breathable material structure 10. The wearer's body surface temperature can be adjusted based on the external temperature sensed through the plurality of sensors 4. When the body surface temperature is too high, the plurality of micro processing chips 3 control the actuation of the plurality of actuating breathable units 2. The breathable effect of gas transportation in a specific direction of the supporting main body 1 is configured to adjust the wearer's body surface temperature. By implementing the actuating breathable material structure 10 on the textile material of the wearing clothes, a smart clothing can be achieved. In an embodiment, when the actuating breathable material structure 10 is implemented as an outer casing of the product (such as an outer casing of a laptop computer), which has heat generated therefrom and required to be dissipated, the plurality of actuating breathable units 2 are compounded in the supporting matrix 11 (such as the outer casing of the laptop computer) of the supporting main body 1 by the method of mixing the plurality of actuated breathable units 2 into a supporting matrix 11 (such as the outer casing of the laptop computer). Moreover, the plurality of micro processing chips 3, the plurality of sensors 4 and the plurality of power supply units are mixed and composed in the supporting matrix 11 (such as the outer casing of the laptop computer) of the supporting main body 1, so as to form the actuating breathable material structure 10. The breathable effect can be adjusted based on the internal temperature (in the outer casing) of the laptop computer sensed through the plurality of sensors 4. When the internal temperature of the laptop computer is overheated, the plurality of micro processing chips 3 control the actuation of the plurality of actuating breathable units 2. By driving the plurality of actuating breathable units 2 to operate, the breathable effect of the supporting main body 1 for transporting the gas in the specific direction is accomplished. An intelligent cooling is achieved.

Accordingly, the actuating breathable material structure 10 of the present disclosure is applied to the product which requires the function of breathability and ventilation. In an embodiment, the actuating breathable material structure 10 forms at least one wearable device. Preferably but not exclusively, the wearable device is at least one selected from the group consisting of a smart phone, a smart bracelet, a smart watch, a wearable blood pressure monitor, a wearable blood glucose meter and a smart clothing. In another embodiment, the actuating breathable material structure 10 forms at least one portable device. Preferably but not exclusively, the portable device is at least one selected from the group consisting of a keyboard, a laptop computer and a display device. In other embodiments, the actuating breathable material structure 10 forms at least one daily necessity. Preferably but not exclusively, the daily necessity is at least one selected from the group consisting of a mask, a baby carriage, a brooch, a button, earrings, a belt, a necklace, sports shoes, glasses, a smart bra, backpacks, pants and clothes. The present disclosure is not limited thereto.

In summary, the present disclosure provides an actuating breathable material structure. By compounding a miniaturized actuating breathable unit in a supporting matrix of a supporting main body, the actuating breathable material structure is formed, so as to be applied to the product which requires the functions of breathability and ventilation. It is industrially valuable.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating breathable material structure, comprising:
   a supporting main body made of a supporting matrix;
   a plurality of actuating breathable units; and
   a plurality of micro processing chips,
   wherein the plurality of actuating breathable units and the plurality of micro processing chips are compounded in the supporting matrix and integrally formed with the supporting matrix in one piece, wherein the plurality of actuating breathable units are controlled by the plurality of micro processing chips to perform gas transportation in a specific direction,
   wherein each of the actuating breathable units comprises an outlet aperture on the supporting main body, and a gas is discharged out through the outlet aperture to perform a breathing effect of the supporting main body, and
   wherein each of the actuating breathable units comprises:
   an inlet layer;
   a flow channel layer stacked on and connected with the inlet layer;
   a resonance layer stacked on and connected with the flow channel layer;
   a chamber layer stacked on and connected with the resonance layer;
   an actuating layer stacked on and connected with the chamber layer;
   an outlet layer stacked on and connected with the actuating layer; and
   a plurality of valves.

2. The actuating breathable material structure according to claim 1, further comprising a plurality of sensors embedded in the supporting matrix for electrical connection with the plurality of micro processing chips, wherein detection data from the plurality of sensors is accessible to the plurality of micro processing chips for transmission, the plurality of sensors detect humidity and temperature outside the supporting matrix, and the detection data is provided to the plurality of micro processing chips, so that the plurality of actuating breathable units are controlled by the plurality of micro processing chips to perform the gas transportation in the specific direction, and the breathing effect of the supporting main body is performed.

3. The actuating breathable material structure according to claim 2, wherein each of the plurality of micro processing chips comprises a data transmission component, which receives the detection data from the plurality of sensors and transmits the detection data to an external receiving device, and the external receiving device displays the detection data.

4. The actuating breathable material structure according to claim 3, wherein the external receiving device is a mobile communication device.

5. The actuating breathable material structure according to claim 1,
   wherein the inlet layer, the flow channel layer, the resonance layer, the chamber layer, the actuating layer and the outlet layer are stacked on each other sequentially, and the plurality of valves are disposed on the inlet layer and the outlet layer.

6. The actuating breathable material structure according to claim 1, wherein the actuating breathable material structure forms at least one wearable device.

7. The actuating breathable material structure according to claim 6, wherein the wearable device is at least one selected from the group consisting of a smart phone, a smart bracelet, a smart watch, a wearable blood pressure monitor, a wearable blood glucose meter and a smart clothing.

8. The actuating breathable material structure according to claim 1, wherein the actuating breathable material structure forms at least one portable device.

9. The actuating breathable material structure according to claim 8, wherein the portable device is at least one selected from the group consisting of a keyboard, a laptop computer and a display device.

10. The actuating breathable material structure according to claim 1, wherein the actuating breathable material structure forms at least one daily necessity.

11. The actuating breathable material structure according to claim 10, wherein the daily necessity is at least one selected from the group consisting of a mask, a baby carriage, a brooch, a button, earrings, a belt, a necklace, sports shoes, glasses, a smart bra, backpacks, pants and clothes.

12. The actuating breathable material structure according to claim 1, wherein the supporting matrix is a raw material, which is a naturally occurring and unprocessed substance.

13. The actuating breathable material structure according to claim 12, wherein the supporting matrix is an intermediate material, which is a processed substrate formed after processing the raw material.

14. The actuating breathable material structure according to claim 13, wherein the supporting matrix is at least one selected from the group consisting of an organic material and an inorganic material.

15. The actuating breathable material structure according to claim 13, wherein the supporting matrix is at least one selected from the group consisting of a metal material, a polymer material, a ceramic material, a composite material, a building material, an electronic material, an aviation material, an automotive material, an energy material and a biomedical material.

16. The actuating breathable material structure according to claim 1, wherein the actuating breathable unit is manufactured from a micro structural material, and has a size ranging from 1 μm to 999 μm.

17. The actuating breathable material structure according to claim 1, wherein the actuating breathable unit is manufactured from a nano structural material, and has a size ranging from 1 nm to 999 nm.

18. The actuating breathable material structure according to claim 1, wherein the plurality of actuating breathable units are made through a micro-electromechanical (MEMS) process, and the plurality of actuating breathable units are arranged in the supporting matrix in a parallel arrangement, a serial arrangement or a serial-and-parallel arrangement.

19. The actuating breathable material structure according to claim 1, wherein the plurality of actuating breathable units are made through a micro-electromechanical process, and the actuating breathable material structure further comprises a plurality of power supply units embedded in the supporting matrix to output power to the plurality of actuating breathable units and the plurality of micro processing chips for driving operation, wherein the power supply unit is an energy-absorbing electric board, which converts optical energy into electrical energy for outputting, or a graphene battery.

20. An actuating breathable material structure, comprising:
  a supporting main body made of a supporting matrix;
  a plurality of actuating breathable units; and
  a plurality of micro processing chips,
  wherein the plurality of actuating breathable units and the plurality of micro processing chips are compounded in the supporting matrix and integrally formed with the supporting matrix in one piece, wherein the plurality of actuating breathable units are controlled by the plurality of micro processing chips to perform gas transportation in a specific direction,
  wherein each of the actuating breathable units comprises an outlet aperture on the supporting main body, and a gas is discharged out through the outlet aperture to perform a breathing effect of the supporting main body, and wherein each of the actuating breathable units comprises: an inlet layer
  comprising an inlet aperture;
    a flow channel layer stacked on and connected with the inlet layer, and having a communication channel in fluid communication with the inlet aperture;
    a resonance layer stacked on and connected with the flow channel layer, and having a central aperture spatially corresponding to the communication channel;
    a chamber layer stacked on and connected with the resonance layer and having a resonance chamber spatially corresponding to the central aperture;
    an actuating layer stacked on and connected with the chamber layer, and comprising an outer region, a vibration region and an actuator, wherein the actuator is disposed on a surface of the vibration region, for being driven in response to an applied voltage to undergo a bending deformation to drive the vibration region to vibrate in a reciprocating manner; and
    an outlet layer stacked on and connected with the outer region of the actuating layer to cover the actuator, and having the outlet aperture, wherein an outlet chamber is formed between the outlet layer and the actuator, and the outlet aperture is in fluid communication with the resonance chamber; and
  a plurality of valves, each of which disposed in the inlet aperture and the outlet aperture to control communication of the inlet aperture and the outlet aperture,
  wherein when the actuator is driven to generate vibration in a reciprocating manner for transporting gas in the resonance chamber, and the plurality of valves are controlled to enable the fluid communication of the inlet aperture and the outlet aperture, the gas is inhaled through the inlet aperture, flows to the resonance chamber, and is discharged out through the outlet aperture, so that the gas is transported in the specific direction, and the breathing effect of the supporting main body is performed.

* * * * *